United States Patent [19]

Jones

[11] 4,248,864

[45] Feb. 3, 1981

[54] REPRODUCTION CONTROL

[75] Inventor: Robert C. Jones, Narberth, Pa.

[73] Assignee: American Home Products Corporation, New York, N.Y.

[21] Appl. No.: 71,207

[22] Filed: Aug. 30, 1979

[51] Int. Cl.³ .................... A61K 37/00; C07C 103/52
[52] U.S. Cl. .............................. 424/177; 260/112.5 R
[58] Field of Search ............... 260/112.5 LH; 424/177

[56] References Cited

U.S. PATENT DOCUMENTS

| 4,010,261 | 3/1977 | Johnson et al. | 260/112.5 LH |
| 4,034,082 | 7/1977 | Johnson et al. | 260/112.5 LH |
| 4,089,946 | 5/1978 | Foell et al. | 260/112.5 LH |

OTHER PUBLICATIONS

A. Corbin, et al., Endocrine Research Communication 3 (6), 359–376, (1976).

Primary Examiner—Delbert R. Phillips
Attorney, Agent, or Firm—Richard K. Jackson

[57] ABSTRACT

A method for denuding a blastocyst by removing its zona pellucida with LHRH or an agonist analogue thereof.

14 Claims, No Drawings

REPRODUCTION CONTROL

BACKGROUND OF THE INVENTION

Luteinizing hormone releasing hormone (LHRH) and agonists thereof have been reported to act as pro-fertility agents in the sense that they induce ovulation in the female. They have been considered also anti-fertility agents because they hyper-stimulate the hypophysial-ovarian steroid axis and prevent implantation of a fertile ovum and maintenance of pregnancy. Corbin et al., End. Res. Comm. 2, 445-458(1975) and 3, 359-376(1976). It is currently believed that these hypothalamic hormones are effective because they trigger the release of luteinizing hormone (LH) from the pituitary, which hormone in turn causes luteolysis, either functional and/or physical, of the corpora lutea (CL) resulting in diminished progesterone release, Hilliard et al., Fert./Steril. 27 421(1976). Depending upon the time of administration, follicle stimulating hormone (FSH) and estradiol-17$\beta$ ($E_2$) levels may be elevated and reduced, respectively, Beattie et al. Biol. Reprod. 16 322(1977). This disruption of normal maternal hormone levels creates a state of incompatability between the fertilized ova and the uterus both prior to and after implantation. To reach that state of abnormal maternal hormone level which assures contraception in actual practice, it is necessary to introduce LHRH or an agonist into the maternal circulation via repeated administration over several days.

LHRH and it's agonists have no direct effect on the uterus of the adult female animal, Humphrey et al., Bio. of Reproduction 19 84-91(1978). The contraceptive application of LHRH and agonists in mechanisms directly involving the pituitary-ovarian steroid axis via the maternal blood system. Although there have been reports of effective anti-pregnancy treatments with single systemic treatments in test models, for practical purposes involving the impossibility of determining that critical point in time when a single systemic administration would be effective in actual practice, repeated dosing over a period of several days has been generally required to insure contraception. Continuous systemic administration of LHRH or an agonist by rectal or vaginal absorption to obtain the desired blood levels necessary to induce ovulation is reported in U.S. Pat. No. 3,917,825.

An LHRH agonist is a compound closely resembling LHRH in structure which operates on the same receptor sites to mimic the activity of LHRH. Examples of a few LHRH agonists known to the art are:

[D-Trp$^6$]LHRH

[D-Trp$^6$-des-Gly-NH$_2$$^{10}$]LHRH ethylamide

[D-Trp$^6$-N-Me-Leu$^7$, des-Gly-NH$_2$$^{10}$]LHRH ethylamide

[D-Ala$^6$-N-Me-Leu$^7$, des-Gly-NH$_2$$^{10}$]LHRH ethylamide and

[D-Ala$^6$, des-Gly-NH$_2$$^{10}$]LHRH ethylamide.

DESCRIPTION OF THE INVENTION

In accordance with this invention there is provided a method for denuding a blastocyst by removal of its zona pellucida which comprises contacting said zona pellucida with LHRH or an agonist analogue thereof.

It has been discovered that the zona pellucida covering a fertilized ovum rapidly disassociates from the blastocyst in the presence of LHRH or an agonist thereof to leave the free blastocyst. The free blastocyst is capable of attachment and implantation in the uterine epithelial tissue of a female mammal. By correctly timing disassociation of the zona pellucida, either a normal pregnancy may be achieved or a premature implantation incompatable with the unprepared uterine epithelium resulting in a non-viable implantation and resorption of the conceptus may result. Hence, LHRH and its agonist analogues can be used in aid of fertilized egg transplant techniques where immediate implantation in the host uterus is desired, by removal of the zona pellucida in vitro followed by transfer of the blastocyst itself to the host uterus which has been accurately prepared and timed by known means for viable implantation of a blastocyst. Thus, current problems of excessive delay in implantation of fertilized ova resulting from the unpredictable period necessary for escape of the blastocyst from its zona pellucida may be overcome by treatment of the fertilized ova with LHRH or an agonist thereof prior to transfer of the blastocyst to the host uterus. In addition, LHRH and its agonist analogues can be used as claudogenic agents by denuding a fertilized ovum in the oviduct (fallopian tubes) or uterine lumen of a female mammal before the uterine epithelium is adequately developed, thereby resulting in no implantation or a non-viable implantation and no pregnancy.

Therefore, in accordance with one aspect of this invention there is provided a method for preventing reproduction which comprises administering a claudogenic amount of LHRH or an agonist thereof into the oviduct or uterine lumen of a female mammal in the presence of the conceptus prior to implantation of the fertilized ovum. The claudogen may be administered into the oviduct or uterine lumen by known means, whether as a liquid solution, foam, aerosol, gel or via a slow-release intrauterine device.

Based upon the prior art evaluation of LHRH agonists lack of direct effect upon the uterus, it is believed, although applicant does not want to be bound by any specific mechanism of action, that LHRH and its agonists act only upon the fertilized ova, during the period of transport in the oviduct and while it is free in the uterine lumen through the state of attachment, but prior to implantation in the uterus.

Pregnancy can be avoided by the presence of LHRH or an agonist thereof in the uterine lumen in an insufficient amount to provide a systemic response (pituitary ovarian axis) during the time the blastocyst is free in the lumen through the attachment period prior to actual implantation. It is to be understood, that although an effective amount of LHRH or an agonist thereof necessary to prevent maintenance of pregnancy is below that demonstrating any systemic response, the amount administered into the uterine lumen or oviduct may well be enough to excite the pituitary systemically without negation of the present invention because sub-systemic amounts are operable and any systemic action on the pituitary-ovarian axis is incidental to achieving the desired result of this invention.

The time sequence of events attending ovulation, ovum transport in the fallopian tubes, fertilization, entry of the blastocyst into the uterine lumen, attachment of the blastocyst to the endometrium and implantation are substantially identical in man and the rat, the latter being a standard animal model for reproductive studies. Thus, in both animal species, considering day 1 the time of ovulation-fertilization, the conceptus (blastocyst) appears in the uterine lumen on about day 4 followed by attachment on day 6, implantation on day 7 and placental formation on about day 12. Based upon that time sequence, the local intra-oviductal or intrauterine application of LHRH or an agonist thereof prevents pregnancy when delivered from day 1 through about day 7 and preferably, in the uterus on day 5 through 7. A single oviductal or intrauterine application of LHRH or an agonist thereof is sufficient to prevent pregnancy although several treatments may be employed in the event that the exact day of fertilization is not known. The dosage to be employed varies with the potency of the polypeptide employed, for example a single intrauterine treatment with 100 $\mu$g of [D-Trp$^6$-N-methyl-Leu$^7$ des-Gly NH$_2$$^{10}$]LHRH ethylamide is sufficient while about 1,000 $\mu$g of LHRH is comparably effective with decreasing potency down to below 100 $\mu$g. Thus, if a single treatment is contemplated employing LHRH, that treatment would employ 1,000 $\mu$g or more to insure effectiveness, while if multiple treatments are contemplated, repeated doses of about 200 $\mu$g of LHRH are sufficient. Furthermore, following a contraceptive approach to prevention of pregnancy, a continuous release device inserted in the oviduct or uterus releasing amounts of LHRH or an agonist well below that required for effective systemic administration, may be employed. An example of one such device may be seen in U.S. Pat. No. 3,898,986, although a large variety of such slow drug release intrauterine devices are known to the art. Suitable matrixes for dispersion and slow release of polypeptides such as LHRH and its agonists, compatable with intrauterine administration are also known in the art, illustrative of which is U.S. Pat. No. 3,880,991.

Unlike contraceptive techniques employing diethyl stilbestrol systemically, which are only effective very early in the stage of fertility (about day 1 to day 4) the process of this invention employing the local application of LHRH or an agonist is also effective later in the period when the fertile ovum is free in the uterine lumen (about day 5). Furthermore, the local administration of LHRH or an agonist thereof produces no toxic symptoms common with the systemic use of diethyl stilbestrol (nausea, vomiting, cramps, headache, etc.). Likewise, any and all undesirable systemic reactions which are induced by LHRH or an agonist may be avoided by the local application of LHRH or an agonist. Menses and luteolysis of the corpus luteum do not occur upon local treatment as they do with systemic use of LHRH and its agonists.

To demonstrate the method for preventing pregnancy by local, intrauterine application of LHRH the following procedure was followed:

Female Charles River CD ® rats (200–210 g) were allowed to cohabit with proven males; the presence of sperm in the vaginal smear was considered day 1 (D1) of pregnancy. In order to lessen the problem of variability between experiments, 5 rats were autopsied at each dose level and the study replicated 3 times to accumulate a total of 15 rats in each experimental group. Luteinizing hormone-releasing hormone was dissolved in 2 $\mu$l of 0.9% NaCl and injected into the right horn of the uterus below the utero-tubal junction between 0945 and 1015 h on D5. One group of control animals received an intrauterine (IU) injection of 2 $\mu$l saline into the right horn on D5. The control animals were autopsied in groups of 5 rats and replicated 3 times to accumulate a total of 15 rats. On D20 the rats were sacrificed, and the uterine horns were divided and weighed individually. The number of viable fetuses as well as the number of placental sites in each horn was recorded. Fetuses from both horns, in control and experimental groups, were examined and weighed individually. A viable fetus is defined as one which compares in anatomical development and weight to a normal control fetus at D20 of gestation. Statistical analysis of the number of viable fetuses and placental sites in each horn was determined by the Kruwalc-Henderson method (Proc. Third Am. Conference of the SAS Users Group International, SAS Institute, Raleigh, North Carolina (1978)); uterine weights of each horn were subjected to analysis of variance (Conover, Practical Nonparametric Statistics, N.Y. John Wiley and Sons, Inc. page 256 (1979)).

The local antifertility data are presented in Table 1. The contents of the injected horn (right) of the control group were unaffected by the administration of 2 $\mu$l saline. However, a significant reduction in the number of viable fetuses in the right horn was obtained with all doses of LHRH. The number of viable fetuses in the right horn was inversely proportional to the dose of LHRH, reaching a low of 0.8 fetuses at a dose of 1000 $\mu$g. The weight of the right horn and its contents also decreased proportionately as the dose of LHRH increased. A significant increase in the number of placental sites was recorded between 200–1000 $\mu$g LHRH.

TABLE 1

Post-Coital Contraceptive Effect of LHRH in the Rat: Effect of Single Intrauterine (Right Horn) Administration on D5 of Pregnancy

| | | Uterine Horn | | | | |
|---|---|---|---|---|---|---|
| | | No. Viable Fetuses (Mean ± S.E.) | | Weight (g) (Mean ± S.E.) | | Placental Scars (Mean ± S.E.) |
| | | Right | Left | Right | Left | Right | Left |
| Vehicle Control (2 $\mu$l Saline) | | 5.3 ± 0.6 | 5.8 ± 0.6 | 18.7 ± 2.0 | 21.9 ± 2.2 | 0.1 ± 0.1 | 0.1 ± 0.1 |
| LHRH | 100 $\mu$g | 3.2 ± 0.3$^a$ | 5.7 ± 0.4 | 12.0 ± 1.0$^b$ | 19.1 ± 1.5 | 0.1 ± 0.1 | 0.1 ± 0.1 |
| | 200 $\mu$g | 1.7 ± 0.4$^a$ | 5.4 ± 0.8 | 6.5 ± 1.3$^b$ | 19.4 ± 2.7 | 1.6 ± 0.5$^c$ | 0.1 ± 0.1 |
| | 300 $\mu$g | 1.5 ± 0.4$^a$ | 6.5 ± 0.6 | 6.9 ± 1.6$^b$ | 21.2 ± 2.3 | 1.3 ± 0.3$^c$ | 0.7 ± 0.6 |
| | 500 $\mu$g | 1.3 ± 0.3$^a$ | 6.1 ± 0.7 | 6.0 ± 0.9$^b$ | 21.8 ± 2.0 | 1.5 ± 0.7$^c$ | 0.5 ± 0.3 |
| | 1,000 $\mu$g | 0.8 ± 0.2$^a$ | 6.9 ± 0.7 | 4.3 ± 0.8$^b$ | 24.3 ± 2.5 | 2.3 ± 0.6$^c$ | 0.3 ± 0.2 |

15 rats/group
$^a$P < 0.05; Right Uterine Horn, LHRH vs. Control.
$^b$P < 0.05; Right Uterine Horn, LHRH vs. Control.
$^c$P < 0.05; Right Uterine Horn, LHRH vs. Control.

There was no significant difference between the left horn of the treated and control group with regard to the number of viable fetuses, weight of the uterus or number of placental sites.

To demonstrate that the antifertility effect observed with intrauterine administration of LHRH is not through absorption into the systemic circulation, LHRH was administered directly into the vagina or via the jugular vein on D5. Autopsy of these two groups followed the above protocol.

Acute administration of LHRH via the jugular vein or vagina produced no negative effects (Table 2). The number of viable fetuses, weight of the uterus and placental sites were unaffected in either horn by LHRH administered by these two routes.

TABLE 2

Effect of Single Intravaginal (Vag) or Intrajugular (IV) Administration of LRH on D5 of Pregnancy

| | | Uterine Horn | | | | | |
|---|---|---|---|---|---|---|---|
| | | No. Viable Fetuses | | Uterine Weight (g) | | Placental Scars | |
| | | Right | Left | Right | Left | Right | Left |
| Saline | Vag | 3.8±0.6 | 6.2±1.4 | 15.4±3.0 | 22.0±5.3 | 0 | 0 |
| LHRH 1,000 | Vag | 7.4±0.8$^a$ | 6.6±0.9 | 21.4±2.0 | 20.5±2.9 | 0.2±0.2 | 0.4±0.2 |
| Saline | IV | 6.8±1.7 | 5.4±0.8 | 23.3±5.3 | 18.6±3.0 | 1.4±1.4 | 0.4±0.4 |
| LHRH 1,000 | IV | 5.4±1.0 | 7.4±0.7 | 18.2±3.9 | 26.3±3.0 | 0.2±0.2 | 0.6±0.2 |

5 rats/group
$^a$P < 0.05; Right Uterine Horn, LHRH vs. Control.

Following the same procedure, [D-Trp$^6$, des-Gly-NH$_2$$^{10}$]LHRH ethylamide (a representative LHRH agonist analogue) was injected into the uterine lumen of the right uterine horn of female Charles River CD ® rats on day 5 after coitus. The status of the pregnancy as indicated by viable fetuses was as follows:

TABLE 3

| | | Viable Fetuses Mean | |
|---|---|---|---|
| No. of Rats | Dose | Right | Left |
| 4 | 1,000 μg | 0.5 | 3.3 |
| 5 | 100 μg | 0.4 | 3.6 |
| 4 | 10 μg | 3.8 | 6.5 |

These results demonstrate the effectiveness of LHRH agonist analogues in preventing reproduction by local action in the uterine lumen of the right urterine horn.

Thus, LHRH and agonist analogues cause a local claudogenic effect when injected into one horn of the uterus on Day 5 of pregnancy. A reduction in the number of viable fetuses is produced in the injected horn and the effect is dose-related. This local claudogenic effect is reflected in the decreased weight of the injected horn and its contents as well as in the increased number of placental sites devoid of fetuses. Conversely, the contralateral horn (uninjected) is unaffected with regard to the number of fetuses, weight of the uterus and placental sites. These results demonstrate that LHRH or an agonist thereof is not being absorbed into the systemic circulation in sufficient quantities to produce a general claudogenic effect.

Previous studies have shown that LHRH does not effect the pregnancy when systemically (s.c.) administered on D5. Humphrey and colleagues (supra) reported that an injection of 1000 μg LHRH on D5 failed to alter the number of viable fetuses or the uterine weight, while Beattie and Corbin, Biol. Reprod., 16 339(1977) have shown that an acute subcutaneous injection of 5000 μg LHRH also failed to inhibit the ensuing pregnancy. In addition, the present study demonstrates that 1000 μg LHRH administered via the jugular vein or vagina on D5 failed to alter the pregnancy in either horn.

McDonald and Beattie, Life Sci. 24, 1103(1979) have shown that LHRH can produce an extra-pituitary interceptive effect in rats hypophysectomized on D12 of pregnancy and suggested that the effect is exerted via the placental:ovarian axis. This study was extended by Bex and Corbin, Endocrine Soc. 61st Ann. Meet. Abstract 436, 181(1979) to include the LHRH agonist, [D-Ala$^6$, des-Gly-NH$_2$$^{10}$]LHRH ethylamide. These authors suggest that the interceptive effect of LHRH and its agonist in hypophysectomized rats may be acting directly on the ovary and/or placental hormones. Also, Hsueh and Erickson, Science 204, 854(1979) have shown that LHRH exerts a direct inhibition of ovarian steroidogenesis. The present invention demonstrates that LHRH can produce an anti-fertility effect prior to implantation through a mechanism other than that involving the hypophyseal-ovarian axis. Luteinizing hormone-releasing hormone may be entering the systemic circulation when injected into the right horn of the experimental animals, but the absence of any effect on the contralateral horn and lack of effect on either horn when administered via the jugular vein or vagina demonstrates that 1000 μg of LHRH is inactive when administered systemically on D5 of pregnancy. Thus, LHRH and its agonist analogues appear to possess an extra-pituitary, local, claudogenic property.

Treatment on the day prior to ovulation through day three, post coitus, in the identical intrauterine manner described above has no observable effect upon the fertilized ova. Attachment, implantation and the complete term of pregnancy procedes without ontoward effect. Again, this demonstrates the absence of any systemic effect because the intrauterine treatment does not effect the ova in the oviduct on days 1–3. However, direct administration of LHRH or one of its agonists into the oviduct prevents successful pregnancy.

Attachment and implantation may occur after treatment of the conceptus with LHRH or an agonist thereof as is indicated by placental sites in the uterus, but successful pregnancy is not maintained. The in situ evidence appears to be consistent with premature escape of the blastocyst from the zona pellucida resulting in premature attachment and non-functional implantation in the unprepared uterine epithelium.

To denude a blastocyst of its zona pellucide in vitro the fertilized ovum is removed from the uterus of the donor animal by known means. The blastocyst is then placed in a small volume of known compatable medium such as physiological saline and LHRH or an agonist is introduced into the medium. The course of removal of the zona pellucida may be readily followed with a microscope and the time period necessary for complete removal of the zona is related to the concentration of the releasing hormone, thereby permitting timed blastocyst release during egg transplant procedures. At 500 μg/μl LHRH in 0.9 percent saline the zona pellucida lyses in about 0.5 minutes; at 50 μg/μl in about 15 to 25 minutes and at 15 μg/μl in about 60 minutes. Recovery of the free blastocyst and transfer to the uterus of a properly prepared and timed mammalion species may then be effected by conventional transfer techniques under optimal timing conditions of both the fertilized egg and the uterine epithelium.

What is claimed is:

1. A method for preventing reproduction which comprises contacting a fertilized ovum surrounded by its zona pellucida in the oviduct or uterine lumen of a female mammal with a claudogenil amount of LHRH or an agonist thereof.

2. The method of claim 1 in which said LHRH or agonist thereof is administered into the oviduct on day 1, 2, 3 or 4 of pregnancy.

3. The method of claim 1 in which said LHRH or agonist thereof is administered to the uterine lumen on day 4, 5, 6 or 7 of pregnancy.

4. The method of claim 3 in which said administration is by single dose on Day 5 of pregnancy.

5. The method of claim 1 in which LHRH or an agonist thereof is administered into the uterine lumen as a foam.

6. The method of claim 1 in which LHRH or an agonist thereof is administered into the uterine lumen as an aerosol.

7. The method of claim 1 in which LHRH or an agonist thereof is administered into the uterine lumen as a liquid solution.

8. The method of claim 1 in which LHRH or an agonist thereof is administered into the uterine lumen via a slow release intra-uterine device.

9. The method of claim 1 in which LHRH or an agonist thereof is administered into the uterine lumen as a gel.

10. The method of claim 1 in which from 0.01 to about 1.0 milligram of LHRH or an agonist thereof is present in the uterine lumen concurrently with a fertilized ovum.

11. The method of claim 1 in which said LHRH or an agonist thereof is continuously released in the uterine lumen from the periovulatory stage to the end of the menstrual cycle.

12. A method for denuding a blastocyst by removal of its zona pellucida which comprises contacting said zona pellucida with LHRH or an agonist analogue thereof.

13. A method for preventing reproduction which comprises administering LHRH or an agonist thereof into the oviduct or uterine lumen of a female mammal in the presence of a conceptus enveloped by its zona pellucida in an amount sufficient to prevent viable implantation of a blastocyst.

14. A method for timing disassociation of the zona pellucida from a conceptus to allow normal attachment, implantation and achieve a normal pregnancy which comprises contacting said zona pellucida with LH-RH or an agonist thereof during that period of mammalian pregnancy at which the conceptus would normally escape its zona pellucida and the uterine epithelium is adequately developed to accept the blastocyst.

* * * * *